US010716518B2

(12) United States Patent
Basu et al.

(10) Patent No.: US 10,716,518 B2
(45) Date of Patent: Jul. 21, 2020

(54) BLOOD PRESSURE ESTIMATION BY WEARABLE COMPUTING DEVICE

(71) Applicant: Microsoft Technology Licensing, LLC, Redmond, WA (US)

(72) Inventors: Sumit Basu, Redmond, WA (US); Daniel Morris, Bellevue, WA (US); Jeremiah Wander, Redmond, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 613 days.

(21) Appl. No.: 15/443,969

(22) Filed: Feb. 27, 2017

(65) Prior Publication Data

US 2018/0116600 A1    May 3, 2018

Related U.S. Application Data

(60) Provisional application No. 62/416,054, filed on Nov. 1, 2016.

(51) Int. Cl.
*A61B 5/00* (2006.01)
*A61B 5/022* (2006.01)
*A61B 5/021* (2006.01)
*A61B 5/0245* (2006.01)
*A61B 5/0402* (2006.01)
*A61B 5/024* (2006.01)

(52) U.S. Cl.
CPC ............ *A61B 5/7267* (2013.01); *A61B 5/022* (2013.01); *A61B 5/0245* (2013.01); *A61B 5/02108* (2013.01); *A61B 5/02438* (2013.01); *A61B 5/0402* (2013.01); *A61B 5/681* (2013.01); *A61B 2560/0223* (2013.01)

(58) Field of Classification Search
CPC .................................................. A61B 5/7267
USPC ........................................................... 703/11
See application file for complete search history.

(56) References Cited

U.S. PATENT DOCUMENTS

| | | | |
|---|---|---|---|
| 4,830,018 A | 5/1989 | Treatch | |
| 6,251,080 B1 | 6/2001 | Henkin et al. | |
| 8,475,370 B2 | 7/2013 | McCombie et al. | |
| 2004/0260185 A1 | 12/2004 | Anderson et al. | |
| 2008/0004904 A1 | 1/2008 | Tran | |
| 2012/0109243 A1 | 5/2012 | Hettrick et al. | |
| 2012/0179055 A1 | 7/2012 | Tamil et al. | |
| 2013/0012823 A1 | 1/2013 | Ripoll et al. | |
| 2013/0041268 A1 | 2/2013 | Rimoldi et al. | |
| 2013/0226010 A1 | 8/2013 | Hotta | |
| 2014/0171749 A1 | 6/2014 | Chin et al. | |
| 2014/0222804 A1 | 8/2014 | Stivoric et al. | |
| 2014/0249398 A1 | 9/2014 | Morris et al. | |
| 2014/0266787 A1 | 9/2014 | Tran | |
| 2015/0106020 A1 | 4/2015 | Chung et al. | |
| 2015/0112208 A1 | 4/2015 | He et al. | |
| 2015/0305632 A1 | 10/2015 | Najarian et al. | |
| 2016/0089033 A1 | 3/2016 | Saponas et al. | |
| 2016/0140834 A1 | 5/2016 | Tran | |
| 2016/0220198 A1 | 8/2016 | Proud | |
| 2016/0287102 A1 | 10/2016 | Saponas et al. | |
| 2016/0287103 A1 | 10/2016 | Saponas et al. | |
| 2016/0287110 A1 | 10/2016 | Morris et al. | |
| 2016/0287172 A1 | 10/2016 | Morris et al. | |
| 2018/0028114 A1* | 2/2018 | Cronin ..................... | A61B 5/16 |

FOREIGN PATENT DOCUMENTS

| | | |
|---|---|---|
| CA | 2887393 A1 | 4/2014 |
| CN | 103529684 A | 1/2014 |
| WO | 2015069940 A1 | 5/2015 |
| WO | 2016065476 A1 | 5/2016 |
| WO | 2016097381 A1 | 6/2016 |

OTHER PUBLICATIONS

Pipke, R. et al., "Feasibility of Personalized Nonparametric Analytics for Predictive Monitoring of Heart Failure Patients using Continuous Mobile Telemetry", In Proceedings of 4th Conference on Wireless Health, Nov. 1, 2013, Baltimore, Maryland, 8 pages.

Asada, H. et al., "Mobile Monitoring with Wearable Photoplethysmographic Biosensors", In Journal of IEEE Engineering in Medicine and Biology Magazine, vol. 22, Issue 3, May 2003, 13 pages.

Dolui, K. et al., "ReTiHA: Real Time Health Advice and Action using Smart Devices", In Proceedings of International Conference on Control, Instrumentation, Communication and Computational Technologies (ICCICCT), Jul. 10, 2014, Kanyakumari District, India, 6 pages.

Chiarugi, F. et al., "Measurement of Heart Rate and Respiratory Rate Using a Textile-Based Wearable Device in Heart Failure Patients", In Journal of Computers in Cardiology, vol. 35, Sep. 14, 2008, 4 pages.

(Continued)

*Primary Examiner* — Jerry Lin
(74) *Attorney, Agent, or Firm* — Alleman Hall Creasman & Tuttle LLP (57) ABSTRACT

According to one aspect of the present disclosure, a method for estimating blood pressure is provided, comprising training a machine learning model on a cohort data set. The cohort data set may include subject-specific contextual data, time-varying features, and blood pressure measurements for a plurality of subjects. The method may include receiving contextual data for a specific subject, wherein the contextual data includes medical history data of the subject. The method may further include personalizing the machine learning model to the subject based on the contextual data. The method may include calibrating the machine learning model to the subject based on a set of time-varying features and blood pressure measurements of the subject. In addition, the method may include using the machine learning model and the time-varying features for the subject to generate a blood pressure estimate.

18 Claims, 5 Drawing Sheets

(56) References Cited

OTHER PUBLICATIONS

Kim, J., "Wearable device heart rate monitoring entering the consumer mainstream", IoT Agenda, TechTarget website, http://internetofthingsagenda.techtarget.com/feature/Wearable-device-heart-rate-monitoring-entering-the-consumer-mainstream, Mar. 2014, 3 pages.

Albaghli, R. et al., "A Vision for Heart Rate Health Through Wearables", In Proceedings of ACM International Joint Conference on Pervasive and Ubiquitous Computing: Adjunct, Sep. 12, 2016, Heidelberg, Germany, 5 pages.

Appelboom, G. et al., "Smart wearable body sensors for patient self-assessment and monitoring", In Archives of Public Health, vol. 72, Published online Aug. 22, 2014, 11 pages.

Yu, C. et al., "Intrathoracic Impedance Monitoring in Patients With Heart Failure—Correlation With Fluid Status and Feasibility of Early Warning Preceding Hospitalization", In Journal of Circulation, vol. 112, Issue 1, Aug. 9, 2005, 9 pages.

Adamson, P. et al., "Hemodynamic Factors Associated With Acute Decompensated Heart Failure: Part 2—Use in Automated Detection", In Journal of Cardiac Failure, vol. 17, Issue 5, May 2011, 2 pages.

Keenan, P. et al., "An Administrative Claims Measure Suitable for Profiling Hospital Performance on the Basis of 30-Day All-Cause Readmission Rates Among Patients With Heart Failure", In Journal of Circulation: Cardiovascular Quality and Outcomes, vol. 1, Sep. 2008, 9 pages.

Fonarow, G. et al., "Risk Stratification for In-Hospital Mortality in Acutely Decompensated Heart Failure—Classification and Regression Tree Analysis", In Journal of the JAMA Network, vol. 293, No. 5, Feb. 2, 2005, 9 pages.

He, D. et al., "Mining high-dimensional administrative claims data to predict early hospital readmissions", In Journal of American Medical Informatics Association, vol. 21, Issue 2, Mar. 2014, 8 pages.

Bettencourt, P. et al., "N-Terminal—Pro-Brain Natriuretic Peptide Predicts Outcome After Hospital Discharge in Heart Failure Patients", In Journal of Circulation, vol. 110, Issue 15, Oct. 12, 2004, 8 pages.

O'Brien, Eoin, "Ambulatory blood pressure measurement", http://www.eoinobrien.org/wp-content/uploads/2008/06/abpm-irish-doctor-1988.pdf, Published on: Sep. 1988, 4 pages.

"ABP Monitoring—Spacelabs Healthcare", http://www.spacelabshealthcare.com/diagnostic-cardiology/abp-monitoring, Retrieved on: Oct. 25, 2016, 2 pages.

"BPro—Radial Pulse Wave Acquisition Device", http://www.bpro.ie/, Retrieved on: Oct. 25, 2016, 5 pages.

"Cardiosign", http://www.cardiosign.com/, Retrieved on: Oct. 25, 2016, 1 pages.

"Finapres Medical Systems", http://www.finapres.com/, Retrieved on: Oct. 25, 2016, 1 pages.

"CNSystems", http://www.cnsystems.at/index.php, Retrieved on: Oct. 25, 2016, 1 pages.

"Arterial Tonometry for Blood Pressure Measurement", https://www.sri.com/engage/products-solutions/arterial-tonometry, Retrieved on: Oct. 25, 2016, 2 pages.

Quick, Darren, "Piezo-resistive fibers enable "e;blood pressure watch"e; with continuous monitoring", http://newatlas.com/blood-pressure-watch/27908/, Published on: Jun. 13, 2013, 4 pages.

"Non Final Office Action Issued in U.S. Appl. No. 15/406,591", dated Nov. 29, 2019, 18 Pages.

* cited by examiner

BLOOD PRESSURE ESTIMATION BY WEARABLE COMPUTING DEVICE

CROSS REFERENCE TO RELATED APPLICATIONS

This application claims priority to U.S. Provisional Patent Application No. 62/416,054, filed Nov. 1, 2016, the entirety of which is hereby incorporated herein by reference.

BACKGROUND

Hypertension, or high blood pressure, is a chronic condition which is generally asymptomatic but is a risk factor for a variety of medically significant outcomes, including stroke, heart failure, and coronary artery disease. It has a large impact on public health and healthcare spending, affecting between 16 and 37% of the world population. Treatment of high blood pressure is readily available via lifestyle changes and medication, but in order to determine who needs such treatment, accurate measurement of blood pressure is a necessity. Even after the initial diagnosis, monitoring blood pressure is helpful for managing hypertension, as doctors can monitor whether patients are keeping their pressure within recommended limits.

Measuring blood pressure (BP) involves determining a systolic (SBP) and diastolic (DBP) value; representing the peak and minimum values of blood pressure in the artery, respectively. The clinical standard of attaining these measurements involves a stethoscope and a sphygmomanometer (inflatable cuff with pressure gauge) and listening for the changes in blood flow as the artery is completely occluded, partially occluded, and unoccluded; this is known as the auscultatory method. Patients will often monitor blood pressure at home with an automated device, also with an inflatable cuff, which uses the oscillometric method of measurement, an approach with a similar principle that attempts to determine the changes in the pressure wave electronically (with some loss in accuracy). These single-point measurements, however, do not necessarily predict whether a patient is truly hypertensive. Blood pressure varies throughout the day, and a patient's blood pressure is often higher at the doctor's office at midday versus when relaxing at home, due both to the physical activity associated with travel to the clinic and the patient's anxiety from meeting with the doctor (known as the "white coat effect").

An increasing body of evidence suggests that ambulatory BP monitoring (ABPM) provides a much more complete measure of blood pressure than either a single measurement at the clinician's office or a single measurement with a home blood pressure device, and as such provides significant value in the diagnosis and treatment of hypertension. The current standard in ABPM is an inflatable oscillometric cuff (typically with a tube going to a base module) that must be worn at all times; the cuff will inflate periodically and at least partially immobilize the wearer's arm. As a result, ABPM studies are logistically difficult; periodic inflation is at best uncomfortable, at worst painful, and often disrupts sleep during overnight studies. This has hindered the adoption of ABPM in practice.

SUMMARY

According to one aspect of the present disclosure, a method for estimating blood pressure is provided, comprising training a machine learning model on a cohort data set. The cohort data set may include subject-specific contextual data, time-varying features, and blood pressure measurements for a plurality of subjects. The method may include receiving contextual data for a specific subject, wherein the contextual data includes medical history data of the subject. The method may further include personalizing the machine learning model to the subject based on the contextual data. The method may include calibrating the machine learning model to the subject based on a set of time-varying features and blood pressure measurements of the subject. In addition, the method may include using the machine learning model and the time-varying features for the subject to generate a blood pressure estimate.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

The inventors of the subject application have considered two non-obtrusive surrogates for oscillometrically-measured brachial pressure in 24-hour BP studies: radial pulse pressure (rPP) and aortic pulse wave velocity (aoPWV). Under certain circumstances, trends in these metrics parallel trends in brachial blood pressure, though an initial calibration measurement is always required. The former (rPP) has been embodied in at least one commercially available device (the HealthSTATS BPro, which is FDA-cleared as an ambulatory blood pressure monitor). The latter (aoPWV) remains a research approach. The inventors have discovered that both approaches suffer from accuracy issues, and that the latter (aoPWV) is not readily observable from a wearable device, which has prevented adoption of either approach as an ABPM replacement.

To address these issues, the inventors conceive that instead of such approaches, potential benefits in accuracy may be realized by incorporating a wide variety of other physiological and contextual factors. For instance, knowing a patient's heart rate, activity state (including recent activity levels), physical pose, time and type of last medication dose, or even static information from their health records (previous smoking history, recent significant weight loss or gain, pregnancy, etc.) can greatly augment the predictive power of a BP model. In this disclosure, a solution that uses machine learning to predict BP values from a broad set of features that can be obtained non-invasively from unobtrusive wearable sensors and other obtainable information is described.

This approach not only provides a more practical solution to ambulatory BP monitoring, but also, given the unobtrusiveness of the required sensing, it opens the door to new types of treatment that involve continuous monitoring over the course of months or years. Some of these possibilities are discussed in the description below.

Figure 1A:
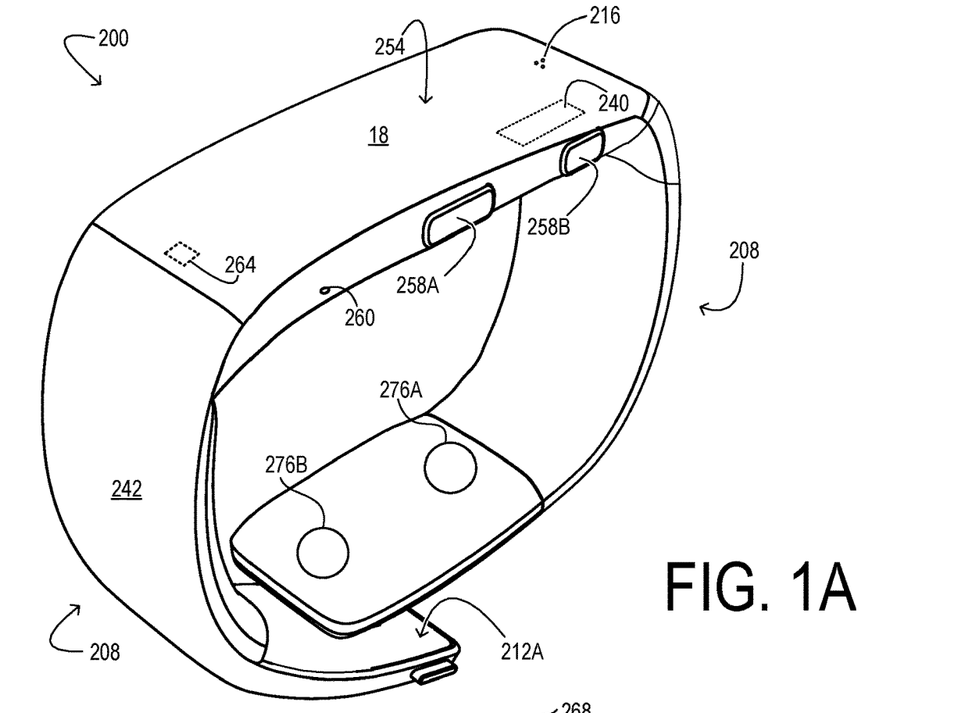
FIGS. 1A and 1B show a wearable sensing device according to examples of the present disclosure.
Figure 1B:
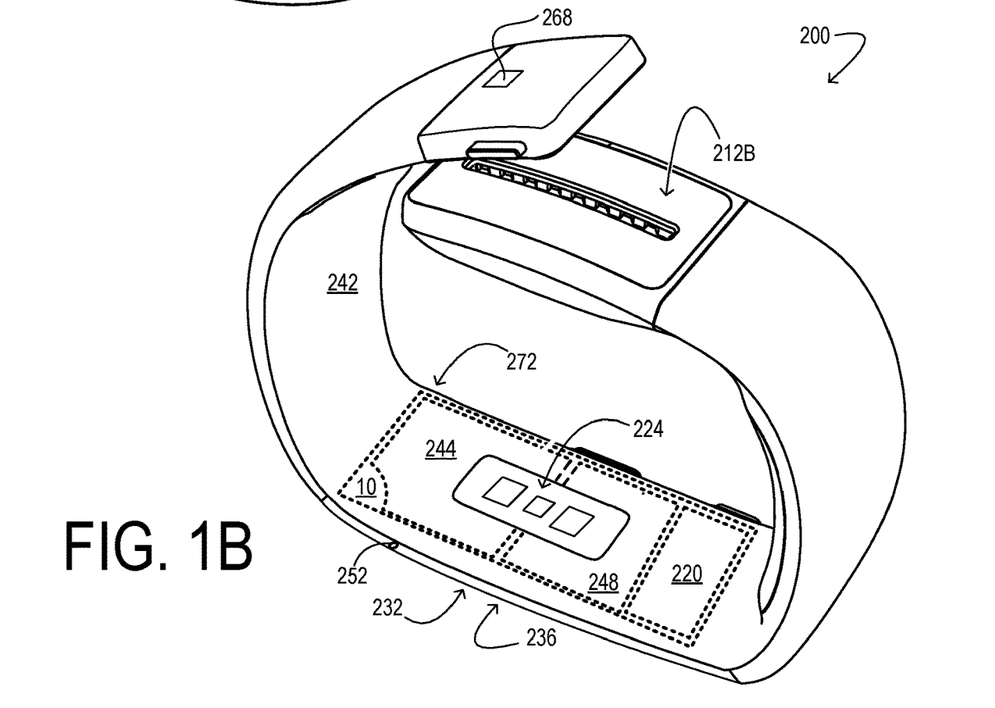

With reference now to FIGS. 1A and 1B, aspects of an example computing device 10 in the form of a wearable sensing device 200 will now be described. In this example wearable sensing device 200 is band-shaped with fastening componentry 212A and 212B arranged at both ends of the device. The fastening componentry enables the device to be closed into a loop and to be worn on a patient's wrist.

Wearable sensing device 200 may include various functional components integrated into the device. For example, the wearable sensing device 200 may include computing device 10, display device 18, a loudspeaker 216, and a communication suite 220. The wearable sensing device 200 may also include various sensors, such as an optical heart rate sensor 224 and motion sensing componentry. The optical heart rate sensor 224 may comprise an optical source configured to illuminate one or more blood vessels through a patient's skin, and an optical sensor configured to measure reflected illumination from the blood vessels. In this manner, measurements of the wearer's heart rate, blood oxygen level, blood glucose level, or other biomarkers with optical properties may be generated.

In some examples the motion sensing componentry may comprise an accelerometer 232 and a gyroscope 236 inside the device 200. In other examples, the motion sensing componentry may comprise any combination of accelerometers 232, gyroscopes 236, and magnetometers.

In some examples the accelerometer 232 and gyroscope 236 may furnish inertial and/or rotation rate data along three orthogonal axes, as well as rotational data about the three axes, for a combined six degrees of freedom (6DOF). This 6DOF sensor data may be used to provide pedometer and calorie-counting functions, for example.

The wearable sensing device also may include a GPS receiver 240 for determining the wearer's geographic location and velocity. In some configurations, the antenna of the GPS receiver may be relatively flexible and extend into side regions 208. The wearable sensing device 200 also may include a barometer 252 for measuring a barometric pressure to which the device is subject.

The above-described components may draw power from one or more energy-storage cells 242. Energy-storage cell(s) 242 may comprise one or more batteries, such as a lithium ion battery.

In wearable sensing device 200, computing device 10 is situated below display device 18 and operatively coupled to the display device 18, along with loudspeaker 216, communication suite 220, and the various sensors. The computing device 10 includes a data-storage machine 244 to hold data and instructions, and a logic machine 248 to execute the instructions.

Display device 18 may be any suitable type of display device. In some configurations, a thin, low-power light emitting diode (LED) array or a liquid-crystal display (LCD) array may be used. An LCD array may be backlit in some implementations. In other implementations, a reflective LCD array (e.g., a liquid crystal on silicon, LCOS array) may be front lit via ambient light. A curved or a flat display may be used. In some examples AMOLED displays or quantum dot displays may be used.

Communication suite 220 may include any appropriate wired or wireless communications componentry. The communication suite 220 may include two-way Bluetooth, Wi-Fi, cellular, near-field communication, and/or other radios. In some implementations, the communication suite 220 may include an additional transceiver for optical (e.g., infrared) communication.

In wearable sensing device 200, a touch-screen sensor 254 is coupled to display device 18 and configured to receive touch input from the user. Pushbutton sensors may be used to detect the state of push buttons 258A, 258B which may include rockers. Input from the pushbutton sensors may be used to enact a home-key or on-off feature, control audio volume, turn the microphone on or off, or other function.

FIGS. 1A and 1B show various other sensors of wearable sensing device 200. Such sensors include microphone 260, ambient light sensor (ALS) 264, UV sensor 268, and ambient temperature sensor 272. The microphone 260 provides input to computing device 10 that may be used to measure the ambient sound level and/or sound pressure profiles, and may receive voice commands from the wearer. Input from one or more of the above-described sensors may be used to assess aspects of the wearer's environment, such as the whether the wearer is indoors or outdoors, temperature, overall lighting level, etc.

FIG. 1A shows a pair of contact sensor modules 276A and 276B that contact the wearer's skin when wearable sensing device 200 is worn. The contact sensor modules may include independent or cooperating sensor elements to provide a plurality of sensory functions. For example, the contact sensor modules may provide an electrical resistance and/or capacitance sensory function, which measures the electrical resistance and/or capacitance of the wearer's skin. At least one contact sensor module is an electrocardiograph 54 configured to detect a pulse electrical signal 56 when the user touches the wearable sensing device 200 with the hand not wearing the device 200 to form a complete circuit that includes the wearable sensing device 200 and the user's heart. In some examples, a contact sensor module may also provide measurement of the wearer's skin temperature. At least one contact sensor module is a pulse pressure sensor 50 configured to detect a pulse pressure wave signal 52.

Figure 2:
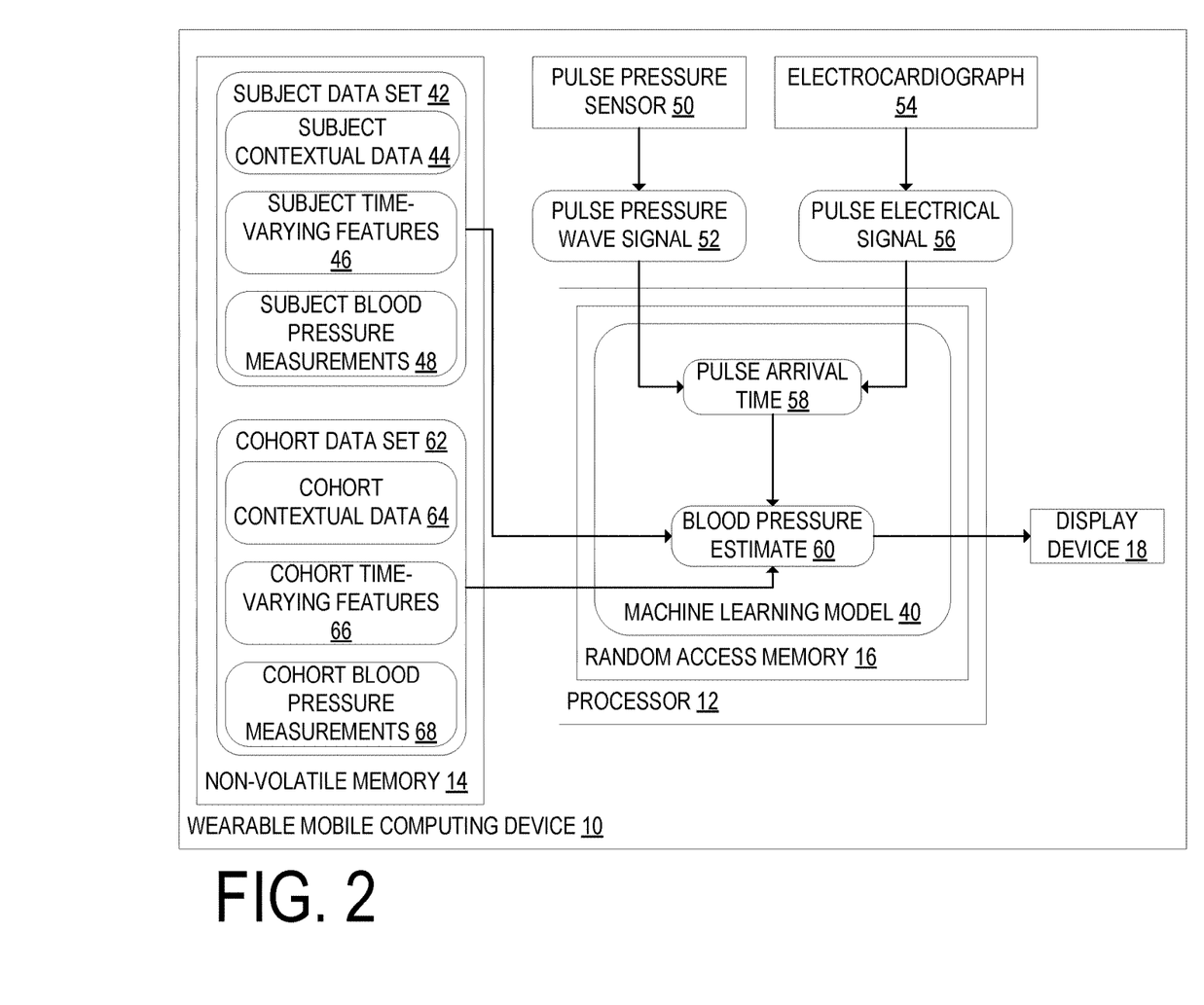
FIG. 2 shows a flow chart illustrating the wearable sensing device producing a blood pressure estimate using a machine learning model, according to examples of the present disclosure.

FIG. 2 shows a wearable sensing device 200, including a processor 12, non-volatile memory 14, random access memory 16, and a display device 18. The processor 12 is configured to use a machine learning model 40 to produce a blood pressure estimate 60 on the random access memory 16. The machine learning model 40 produces the blood pressure estimate 60 using data stored in the non-volatile memory 14. The machine learning model 40 may convey the blood pressure estimate 60 for display on a display device 18.

The data with which the machine learning model 40 makes the blood pressure estimate 60 includes a subject data set 42. The subject data set 42 may include contextual data 44, time-varying features 46, and blood pressure measurements 48. The contextual data 44 includes medical history data of the subject. The subject contextual data 44 of the subject may include information from the subject's medical history data selected from the group consisting of demographic information, comorbidities, past and present medications, vital signs, laboratory test results, recent weight change, echocardiogram results, cardiovascular disease history, smoking history, and past and present pregnancy.

The machine learning model 40 also makes the blood pressure estimate 60 based on a cohort data set 62. The cohort data set 62 includes subject-specific contextual data 64, time-varying features 66, and blood pressure measurements 68 for a plurality of subjects. The cohort contextual data 64 may include medical history data of the subjects in the cohort. The medical history data included in the cohort contextual data 64 may include information from the subjects' medical history data selected from the group of features listed above.

The wearable sensing device 200 of the present disclosure may combine static data (measured in the clinician's office, obtained from medical records, or entered by the patient) and dynamic data (measured by the wearable sensing device 200) into a blood pressure estimate 60 using the machine learning model 40.

The static data may include calibration data, which may contain measurements both from the device 200 and a conventional blood pressure measurement (via auscultatory method, oscillometric cuff, etc.). The calibration data can be used to modify the blood pressure estimate 60 using the machine learning model 40.

The calibration data may be more effective if it contains a range of blood pressure values. In order to achieve this, the subject can be led through a number of postural variations (standing, sitting, lying down) in order to capture this variation.

Variation in the blood pressure values for the calibration data can also be achieved via exercise, such as walking on a treadmill or riding a stationary bicycle.

Variation in the blood pressure values for the calibration data can also be achieved via pharmacological intervention, i.e., measurements can be taken before and after (e.g., at 10 minute intervals) taking a dose of blood pressure-lowering medication.

The processor 12 is configured to receive input from a pulse pressure sensor 50. The pulse pressure sensor 50 is configured to detect a pulse pressure wave. Upon detecting a pulse pressure wave, the pulse pressure sensor 50 inputs a pulse pressure wave signal 52 into the processor 12.

The processor 12 may also be configured to receive input from an electrocardiograph (EKG) 54. The EKG 54 may be configured to detect a pulse electrical signal 56. Upon detecting a pulse electrical signal 56, the EKG 54 may input the pulse electrical signal into the processor 12.

Based on at least the pulse pressure wave signal 52 and the pulse electrical signal 56, the machine learning model 40 may determine a pulse arrival time 58. The pulse arrival time 58 is the time difference between the time at which a heartbeat is detected in the pulse electrical signal 56 and the time at which the same heartbeat is detected in the pulse pressure wave signal 52.

The machine learning model 40 may also determine a variety of pressure wave morphology metrics based on the pulse pressure wave signal 52. The pulse pressure sensor 50 may be configured to detect the pressure wave morphology of the pulse pressure wave signal 52, including pressure wave morphology metrics selected from a group consisting of augmentation index, maximum systolic slope, systolic rise time, ejection time, dicrotic notch height, dicrotic notch time, pulse pressure, reflected wave arrival time, and heart rate.

The wearable sensing device 200 may detect a variety of conditions under which the patient's blood pressure is likely to change. Based on detecting such conditions, the machine learning model 40 may compare the blood pressure of the patient to the blood pressure that the patient had previously under similar conditions.

For example, a large fraction of people exhibit a phenomena known as "nighttime dipping," in which the blood pressure drops significantly during the night. The wearable sensing device 200 may detect a time of day and input the time of day into the machine learning model 40. Based on the inputs of the sensors of the wearable sensing device 200, the wearable sensing device 200 may also be configured to detect when the patient is asleep, and when the patient is asleep detect a sleep stage. These detections of sleep and sleep stage may be used as inputs by the machine learning model 40.

The wearable sensing device 200 may also detect physical activity of the patient. Physical activity that changes heart rate affects blood pressure differently than other factors; thus it is important both to estimate the level of physical activity over time and to model the ways in which it can affect blood pressure. The wearable sensing device 200 may detect that the patient is engaging in physical activity by, for example, detecting a signature reading from an accelerometer 232 in conjunction with an increase in heart rate. The machine learning model 40 may use the detection of physical activity as an input. Medium- to long-term use of the wearable sensing device 200 can show a patient's overall level of physical activity and physical activity patterns, which can provide another set of contextual factors for blood pressure.

Blood pressure can vary significantly based on location, due both to the physical activity required to travel between locations and changes in stress or alertness associated with changes in location. The wearable sensing device 200 may be configured to detect the location of the patient, for example using a GPS receiver 240. The machine learning model 40 may use the location of the patient as an input.

The pose of the patient's body can also affect the patient's blood pressure. The wearable sensing device 200 may be configured to detect the body pose of the patient. For example, the wearable sensing device 200 may determine the patient's body pose by using the accelerometer 232 and the gyroscope 236 to detect the acceleration and spatial orientation of the wearable sensing device 200. For example, the wearable sensing device 200 may use recent data from the accelerometer 232 and gyroscope 236 to determine whether the patient is sitting, lying, standing, or walking. A body pose detected using these or other inputs may be used as an input by the machine learning model 40.

The machine learning model 40 may use a variety of machine learning techniques. Machine learning techniques used by the machine learning model 40 to generate the blood pressure estimate 60 may include regression models, hidden Markov models, conditional random field models, and other models.

In one instantiation, the machine learning model 40 may be a regression model that uses as input static features and dynamic features to estimate BP values at a given time, but does not make use of dynamic feature history prior to that window. This approach may be useful when typical models of time variation learned from a larger cohort could prove deleterious to predictive power, especially for patients who have minimal contextual data or are being monitored for a short time.

In another instantiation, the machine learning model 40 may be a time-series model using features from both the current timestep and history, with a Markov assumption. A Markov assumption is an assumption that all the dependence in previous timesteps is captured in the previous model output (e.g., in a Hidden Markov Model). With this assumption, to predict blood pressure at time t, the machine learning model 40 only needs to use dynamic features associated with time t, along with the probabilities of various blood pressures from time t−1. Static features may be re-incorporated at each time step, or static features may factor explicitly only into the initial output t0 (they would then be implicitly carried forward in model output). This restriction can be relaxed to include other information from recent timesteps (e.g., in conditional random field models).

For either regression or time series models, the machine learning model 40 need not be restricted to a generic combination of features. There is great modeling power in introducing a small number of person-specific parameters into the model, which can be fit based on static (EMR, etc.) data and/or a small number of cuff-based calibration measurements.

It is possible to go beyond generic/agnostic machine learning models to incorporate specific elements of physiological models into the machine learning model 40. For instance, one well-known model of blood pressure is as follows:

$$BP = CO*SVR = (HR*SV)*SVR$$

where CO is cardiac output, SVR is systemic vascular resistance, HR is heart rate, and SV is stroke volume. This particular model can help distinguish the effect of exercise versus other endogenous factors on blood pressure. Since particular features may be more relevant to some of these entities than others, these relationships can be expressed directly in a model, e.g.:

$$SVR = \Sigma w_{si} f_{si}$$

$$SV = \Sigma w_{vi} f_{vi}$$

$$BP = HR*SV*SVR$$

where $f_{si}$ and $f_{vi}$ are features expected to be of value in predicting SVR and SV, respectively. While knowing the nature of the interaction between these intermediate variables will be valuable, it is not necessary to know the specific contributions of the feature variables (i.e., the weights). Note that the linear model for each subcomponent is only meant as an illustration; nonlinear instantiations are also possible.

An example embodiment of a machine learning model 40 is provided below. At a high level, the model of interest uses a mapping that can be described as:

$$y_{it} = F(x_{it}, x_{is}, \theta_i, \theta_g)$$

Above, $x_{it}$ represents time-dependent features available to the model for a subject i at a time t (possibly including information from previous timesteps), $x_{is}$ represents static features for the subject, and $y_{it}$ represents a target variable (e.g., systolic blood pressure) at a given timestep. Parameters $\theta_g$ refer to global parameters pertaining to all subjects, and $\theta_i$ refer to parameters specific to a particular subject.

To train such a model, the model optimizes the mapping over all parameters with all training data (i.e., all subjects in a training set):

$$\Theta_{opt} = \operatorname*{argmin}_{\Theta} \sum_{train} L(F(x_{it}, \theta_i, \theta_g), y_{it})$$

where L(•,•) is a loss function, for instance squared loss:

$$L(a,b) = (a-b)^2$$

When a new subject (unseen to the model) is introduced, the model is modified in two ways. First, the static features for the subject are used to determine the $\theta_i$ parameters:

$$\theta_i = G(x_{is})$$

Second, some or all of the $\theta_i$ parameters can be optimized for the subject using calibration data, with $\theta_g$ held fixed (this is the more conventional form of model personalization):

$$\theta_{i,opt} = \operatorname*{argmin} \sum_{calibration} L(F(x_{it}, \theta_i, \theta_g), y_{it}) + Z(\theta_i, \theta_{ig})$$

In the above Z represents an optional penalty term for straying too far from learned $\theta_i$ values in the in the training data. The examples below illustrate how this can be done in practice, though the particular mechanisms should not be considered exclusive, i.e., many other modeling choices are available within this same framework.

One example of the model described above makes use of linear regression, a very simple "inner model," as the core of the approach.

$$y_{it} = w^T x_{it} + b$$

Where w is of length Q, i.e., there are Q time-dependent features available at every timestep, which may include information from previous timesteps. Note that w and b are global to all subjects.

In this simple form, it will be very difficult for this model to perform well, especially for a signal such as blood pressure. Since the baseline values and dynamic range of blood pressure for different subjects vary greatly, the model will have to try to make the best average fit over all of these variations, and in the end will learn a set of parameters that is not particularly effective for any subject.

To counter this issue, the inner model may now be augmented with additional subject-specific parameters. The simplest version of this would be the addition of a subject-specific bias term; a further step would be to add a subject-specific scaling term. Both are incorporated in the model below:

$$y_{it} = \alpha_i (w^T x_{it}) + \beta_i$$

These additional parameters can be fit using a small number of calibration measurements $x_{it,c}$, $y_{it,c}$ given the calibration equation for $\theta_{i,opt}$ above. In addition, w may be adjusted based on these calibration measurements, though it is critical to use the penalty term Z in that case to prevent overfitting.

The scale and bias parameters above greatly improve the ability of the model to fit the range of a new subject's data, and while the regression parameters w may be tuned with calibration data and the penalty term, the true model could go beyond this to use a variety of modes of parameters. For instance, subjects of a particular gender, weight, or medical history may have a different characteristic set of parameters. Furthermore, mixtures of such modes could provide even greater coverage. Given such a set of modes, the static measurements $x_{is}$ could be mapped to an appropriate mode or mixture of modes.

One approach to mapping the static measurements $x_{is}$ to an appropriate mode or mixture of modes would be to fit subject-specific regression models for a large number of subjects and then cluster the resulting set of regression parameter sets $w_0 \ldots w_N$. A separate set of classifiers may then be used to identify cluster membership for new individuals based on their static measurements $x_{is}$. The parameters of a chosen cluster may then be used for the subject. This approach would require a large number of subject-specific fits in order to discover meaningful clusters, and it would not be known whether predicting cluster membership effectively based on $x_{is}$ would be possible, as the $x_{is}$ would be disconnected from the clustering.

Another approach would be to use principal component analysis (PCA) or another dimensionality reduction approach on the set of learned regression parameters $w_0 \ldots w_N$ as a low-dimensional characterization of the space of valid regression parameters, and then use the calibration data to fit coefficients for the characterization. The characterization would fit into the penalty term Z, as for instance with PCA the underlying Gaussian model of the parameter space would make for an effective prior or penalty (i.e., using negative log likelihood of this model). With only a small number of measurements, either only a very small number of modes could be used, or there would need to be heavy reliance on the penalty term to prevent overfitting. Furthermore, while in principle a second regression model could be trained mapping $x_{is}$ to $\theta_i$, there is no guarantee the second regression model would be effective, since the modes would have been fit independently of the static measurements.

A model that simultaneously estimates the mapping function between $x_{is}$ and $\theta_i$ as well as the parameters $\theta_g$ and jointly optimizes the overall loss on all the training data for all subjects is shown below. This model results in modes that are predictable from $x_{is}$ because the modes were trained in this manner. Furthermore, the model has a flexible number of modes that can be tuned given the amount of data available for training. Both of these goals can be achieved with the following joint model, where a vector of responsibilities $\pi$ creates a convex combination of M modes (the $w^k$, each of which is a full set of parameters for the inner model) to form $w_i$:

$$w_i = \pi_i \begin{bmatrix} w^0 \\ w^1 \\ \vdots \\ w^{M-1} \end{bmatrix} = \pi_i W$$

The parameters $\pi_i$ are in turn formed from the static features $x_{is}$ through a mixture parameter regression matrix P with rows $P_j$. The outputs are constrained to be both positive and sum to one:

$$\pi_{i,j} = \frac{\exp(P_j x_{is})}{\sum_j \exp(P_j x_{is})}$$

Once the number of modes M has been chosen, the mode matrix W and the P matrix have a total number of MQ+MC global parameters with two additional scale and shift parameters ($\alpha_i$ and $\beta_i$) specific to each subject. For a particular subject, the $x_{is}$ may be input into the above equation to determine the mode weights $\pi_i$ and with these compute a convex combination of $w^k$ to produce $w_i$. The scale and shift parameters $\alpha_i$ and $\beta_i$ can be fit with calibration data for that subject.

A diagram of the personalized prediction model described above is shown in FIG. 3. The personalized prediction model 80 operates in four stages, including a training stage, a personalization stage, a calibration stage, and a runtime stage. In the training stage, the personalized prediction model 80 takes as inputs the subject-specific static data $x_{is}$ and the time-dependent data and targets $x_{it}$, $y_{it}$ for all subjects in the training data and fits matrices W and P (these are the global parameters of the model).

Figure 3:
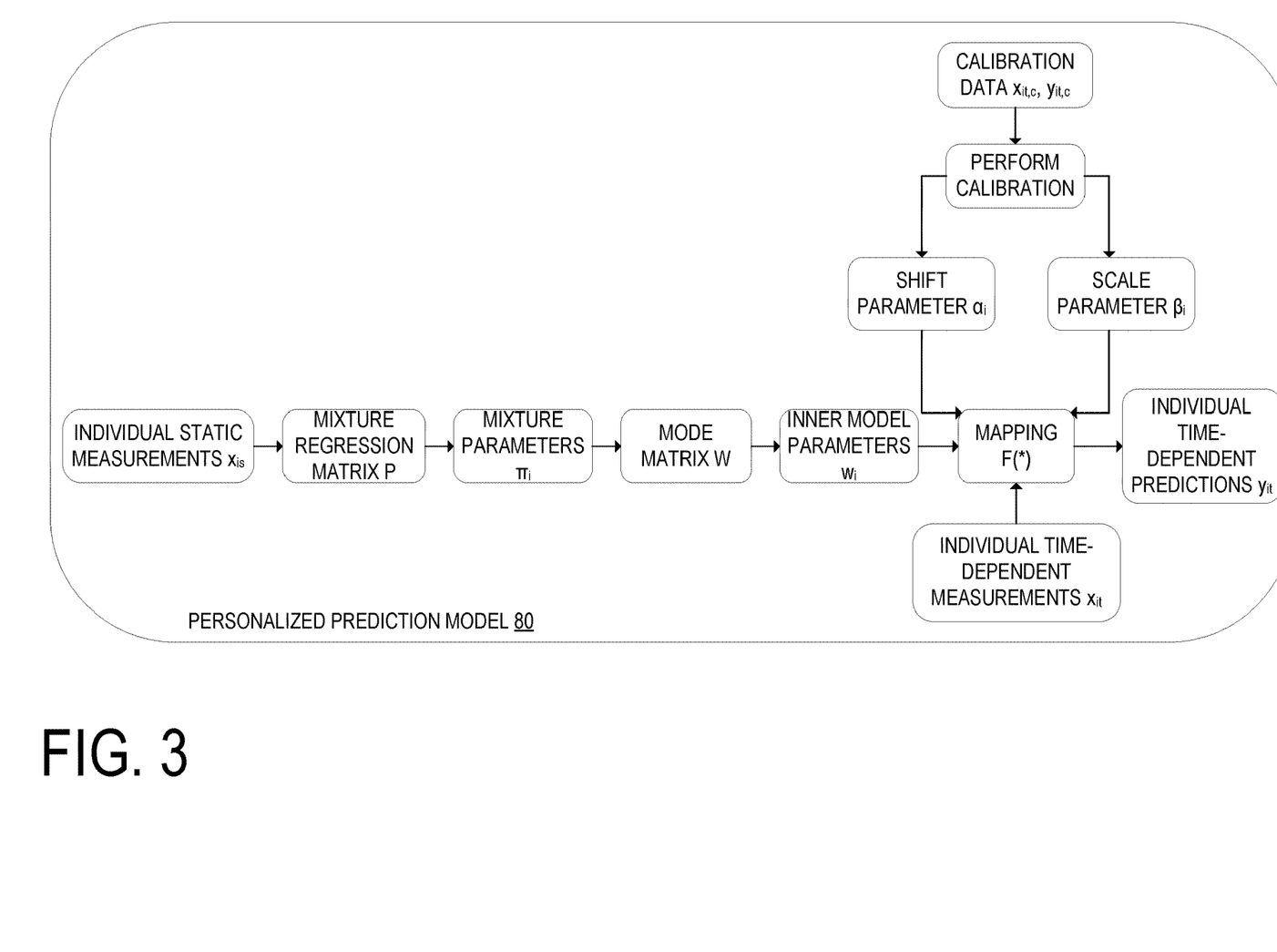
FIG. 3 shows a flow chart illustrating a machine learning algorithm according to examples of the present disclosure.

In the personalization stage, the personalized prediction model 80 takes as inputs the static data $x_{is}$ from one subject and uses the subject's static data $x_{is}$ to determine mixture parameters $\pi_i$ via mixture parameter regression matrix P and the normalization described above; these $\pi_i$ are then applied to mode matrix W to generate the inner model parameters $w_i$ for that subject.

In the calibration stage, the personalized prediction model 80 takes as inputs the calibration data $x_{it,c}$ and $y_{it,c}$. From the calibration data, the personalized prediction model 80 generates a scale parameter $\alpha_i$ and a shift parameter $\beta_i$. These parameters are used to modify the mapping F(*).

In the runtime stage, the personalized prediction model 80 uses the parameters generated in the previous three stages, which are now fixed for the subject, to generate personalized time-dependent predictions $y_{it}$ from that subject's time-dependent measurements $x_{it}$.

Once a blood pressure estimate 60 has been generated, the wearable sensing device 200 may modify the schedule on which measurements of the inputs of the machine learning model 40 are taken based on the blood pressure estimate 60. The wearable sensing device 200 may use physiological data, along with clinical data and patient-reported symptom data, not only to predict outcomes, but also to change the rate and timing at which physiological measurements and symptom reports are taken. For example, if the machine learning model 40 generates identifies signs of dangerous levels of blood pressure but has low confidence in this prediction, the frequency of measurement of both symptom report data and physiological data can be increased; in contrast, if the model indicates that the patient is emerging from a high-risk period and appears to be stable, the frequency of data collection can be reduced to improve compliance and reduce patient burden. As a second example, when patients report symptoms that present only during exercise or activity, or if the machine learning model 40 identifies this automatically, measurement resources can be allocated to times of higher activity.

The wearable sensing device 200 is primarily a wrist-worn sensing device, but also offers the opportunity to incorporate other elements of heart failure monitoring and management via notifications and data input on the wearable sensing device 200. For example, the device 200 can provide medication reminders, possibly coupled specifically to the detection of medication ingestion described below. That is, because medication ingestion can be specifically detected, the device 200 can provide reminders that are only surfaced when a patient misses a dose. Similarly, because the machine learning model 40 can present early indicators of changes in blood pressure, the device 200 may also provide intelligent reminders of behavioral instructions (e.g. dietary restrictions) when it appears that that patient is at high risk of a spike/dip in blood pressure.

After the machine learning model 40 has determined a blood pressure estimate 60, the machine learning model 40 may produce a variety of outputs based on the blood pressure estimate 60. For example, the blood pressure estimate 60 may be conveyed for display on a display device 18.

The machine learning model 40 may also convey the blood pressure estimate 60 for display to a clinician. The blood pressure estimate 60 may be conveyed to the clinician as a direct presentation including the systolic and diastolic blood pressure. It may also be conveyed to the clinician in the form of alerts or continuously varying risk scores and risk score predictions. For example, based on outputs conveyed by a plurality of wearable sensing devices 200 used by a cohort of patients, blood pressure estimates 60 may be conveyed to the clinician in the form of a dashboard of all patients in the cohort, with each patient's risk of becoming hypertensive in the next month, year, etc. even if they are not hypertensive at the moment.

The blood pressure estimate 60 may also be used to track the effectiveness of medications taken by the user. Medications typically given to blood pressure patients (e.g. ACE inhibitors, angiotensin II receptor antagonists, aldosterone antagonists, diuretics) have a significant acute effect on blood pressure that can be observed based on the blood pressure estimate 60. As such, the machine learning model 40 can be used to monitor whether the medication was taken, whether it is working as expected, whether the dose was too low/high, etc. This information could be used to inform the clinician that medications are working or not working as well as to remind a patient to take medication.

The machine learning model 40 may also model the effect of medications on blood pressure. Different medications have different levels of effect on different patients, and clinicians typically rotate through the possibilities in the hopes of finding the most effective one with minimal side effects. Using the machine learning model 40, beyond simply tracking the changes in medication, if the medication types and ingestion times are available to the system, (e.g. via patient entry on the device or online, or automated mechanisms such as detection of RFID tags on medication bottles), effects of various medications specific to a given patient could be modeled, and as such guide clinicians in predicting appropriate doses. Furthermore, a subset of potential side effects (e.g. lethargy, cardiovascular effects such as rapid heart rate (tachycardia), and shortness of breath) could be tracked automatically.

The machine learning model 40 may also be used to track compliance with and model the effects of non-medication-based interventions. Wearable sensors allow the wearable sensing device 200 to track compliance with non-medication recommendations, such as exercise, reduction of sedentary behavior, light exercise/walking after meals, etc. Furthermore, the machine learning model 40 can model the effectiveness of these interventions both in terms of compliance (not all recommendations will have equal compliance) and in terms of BP effects when executed as recommended. The resulting models can be used by the clinicians to adjust or reinforce their recommendations.

The blood pressure estimate 60 output by the machine learning model 40 may be directly incorporated into treatment decisions. The machine learning model 40 may make automatic or recommended adjustments to medication doses based on the blood pressure estimate 60. The blood pressure estimate 60 may also be used to recommend scheduling of inpatient or outpatient visits.

Figure 4:
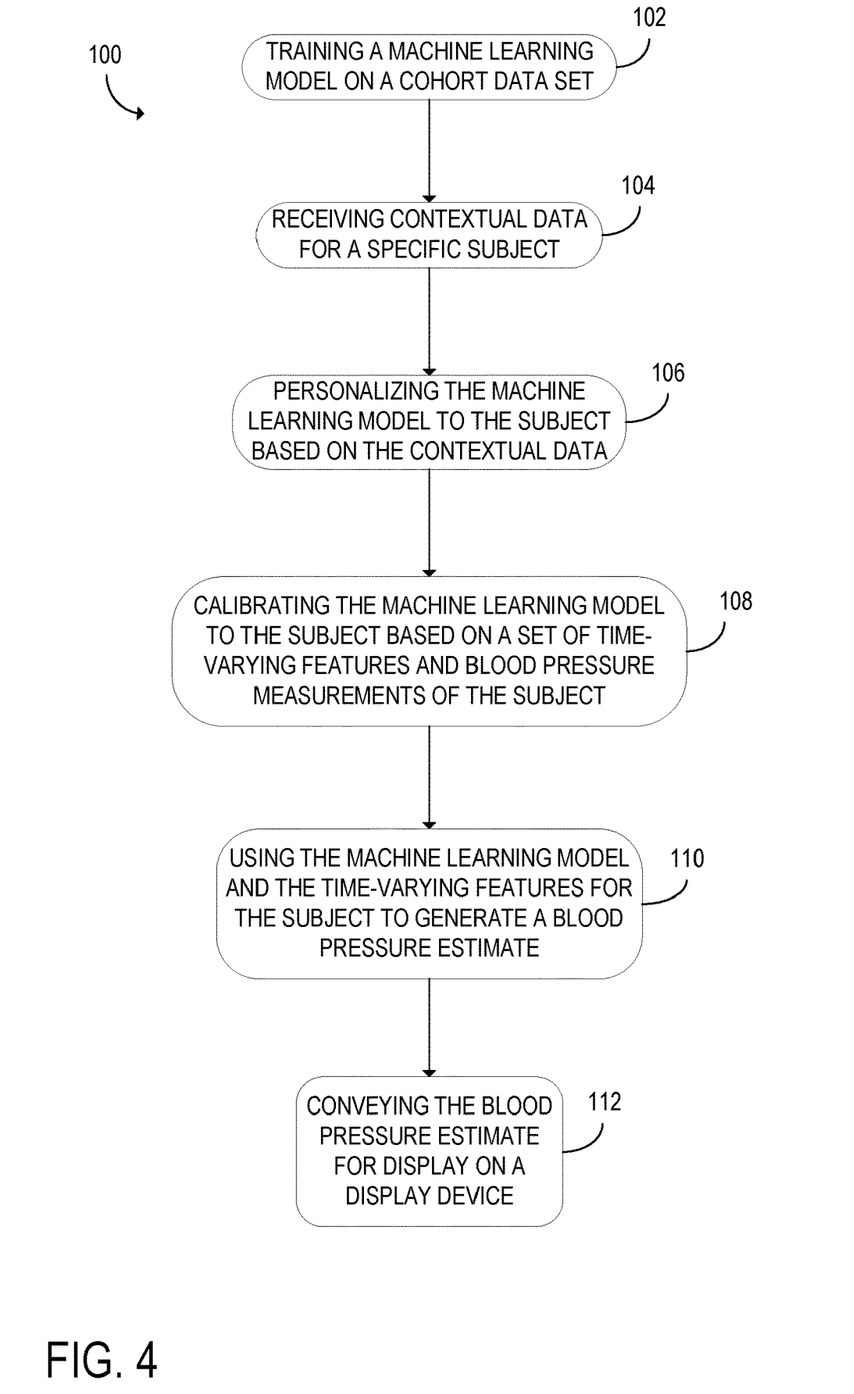
FIG. 4 shows a flow chart illustrating a method for producing a blood pressure estimate.

A method 100 for determining an estimate of the blood pressure of a patient is shown in FIG. 4. The method may be performed using the hardware and software components described above, or other suitable hardware and software components. At step 102, the machine learning model 40 is trained on a cohort data set 62. The cohort data set 62 includes subject-specific contextual data 64, time-varying features 66, and blood pressure measurements 68 for a plurality of subjects in the cohort. The contextual data 64 for the subjects in the cohort may include medical history data.

At step 104, the machine learning model 40 receives contextual data 44 for a specific subject. The contextual data 44 includes medical history data of the subject. The medical history data of the subject may be selected from the group consisting of demographic information, comorbidities, past and present medications, vital signs, laboratory test results, recent weight change, echocardiogram results, cardiovascular disease history, smoking history, and past and present pregnancy. Other patient medical history data may also be used. At step 106, the machine learning model 40 is personalized to the subject using the contextual data 44. The subject-specific contextual data 44 may be used to determine parameters of the machine learning model 40.

At step 108, the machine learning model 40 also receives a set of time-varying features 46 and blood pressure measurements 48 of the subject. This set of data, along with the contextual data 44 of the subject, is used to calibrate the machine learning model 40. The machine learning model 40 may be calibrated at least in part using a brachial cuff measurement. The machine learning model 40 may also be calibrated at least in part by the subject going through a series of perturbations based on posture, exercising at varying levels of intensity, and/or taking medication which changes the blood pressure of the subject.

The time-varying features 46 for the subject may be detected by a wearable sensing device 200. The wearable sensing device 200 may detect a pulse pressure wave signal 52 using a pulse pressure sensor 50 and may detect a pulse electrical signal 56 using an electrocardiograph (EKG) 54. The pulse pressure sensor 50 may be configured to detect the pressure wave morphology of the pulse pressure signal, including pressure wave morphology metrics selected from a group consisting of augmentation index, maximum systolic slope, systolic rise time, ejection time, dicrotic notch height, dicrotic notch time, pulse pressure, reflected wave arrival time, and heart rate. The set of time-varying features 46 for the subject may include a pulse arrival time 58. The pulse arrival time 58 may be determined using the pulse pressure wave signal 52 and the pulse electrical signal 56. The pulse pressure sensor 50 may also detect other pressure wave morphology metrics.

At step 110, the machine learning model 40 and the time-varying features 46 for the subject are used to generate a blood pressure estimate 60. Machine learning techniques used by the machine learning model 40 to generate the blood pressure estimate 60 may include regression models, hidden Markov models, or conditional random field models, as well as other models. At step 112, the blood pressure estimate 60 generated by the machine learning model 40 is conveyed for display on a display device 18.

Figure 5:
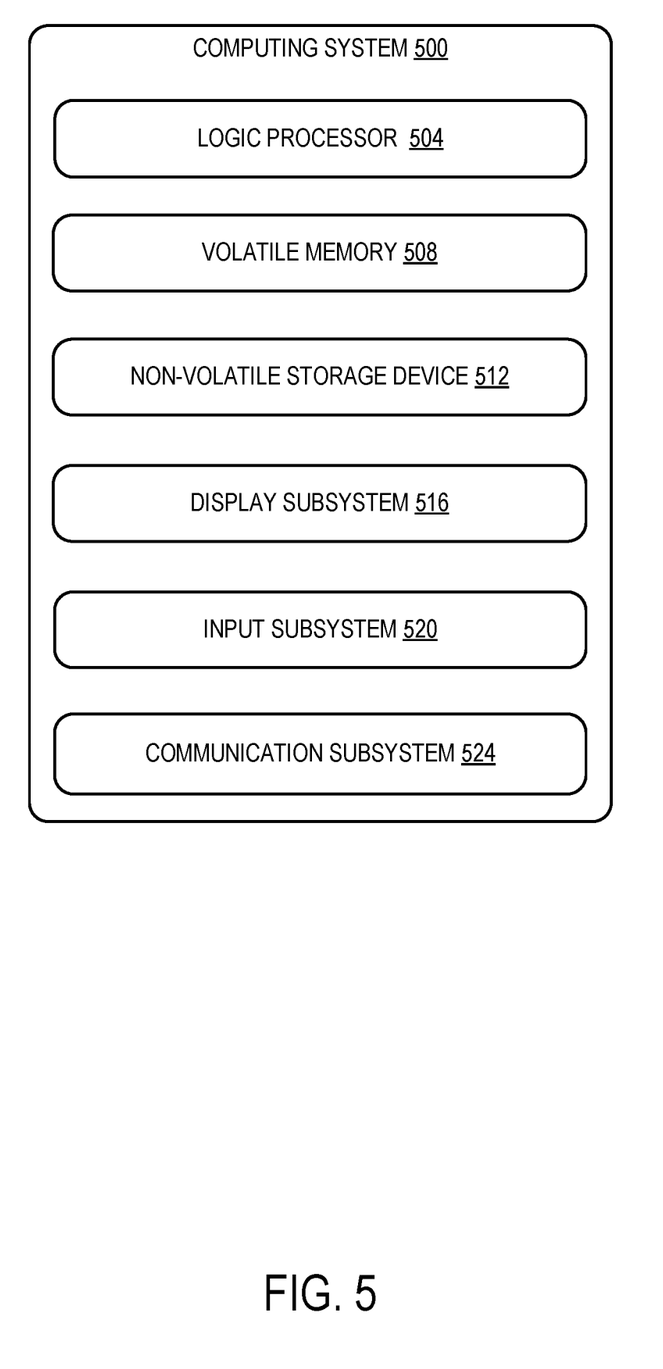
FIG. 5 schematically shows a computing system according to examples of the present disclosure.

FIG. 5 schematically shows a non-limiting embodiment of a computing system 500 that can enact one or more of the methods and processes described above. Computing system 500 is shown in simplified form. Computing device 10 shown in FIG. 1A and FIG. 1B may take the form of computing system 500.

Computing system 500 includes a logic processor 504, volatile memory 508, and a non-volatile storage device 512. Computing system 500 may optionally include a display subsystem 516, input subsystem 520, communication subsystem 524, and/or other components not shown in FIG. 5.

Logic processor 504 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor 504 may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 504 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor 504 may be virtualized and executed by remotely accessible, networked computing devices configured in a cloud-computing configuration. In such a case, these virtualized aspects may be run on different physical logic processors of various different machines.

Volatile memory 508 may include physical devices that include random access memory. Volatile memory 508 is typically utilized by logic processor 504 to temporarily store information during processing of software instructions. It will be appreciated that volatile memory 508 typically does not continue to store instructions when power is cut to the volatile memory.

Non-volatile storage device 512 includes one or more physical devices configured to hold instructions executable by the logic processors to implement the methods and processes described herein. When such methods and processes are implemented, the state of non-volatile storage device 512 may be transformed—e.g., to hold different data.

Non-volatile storage device 512 may include physical devices that are removable and/or built-in. Non-volatile storage device 512 may include optical memory (CD, DVD, HD-DVD, Blu-Ray Disc, etc.), semiconductor memory (ROM, EPROM, EEPROM, FLASH memory, etc.), and/or magnetic memory (hard-disk drive, floppy-disk drive, tape drive, MRAM, etc.), or other mass storage device technology. Non-volatile storage device 512 may include nonvolatile, dynamic, static, read/write, read-only, sequential-access, location-addressable, file-addressable, and/or content-addressable devices. It will be appreciated that non-volatile storage device 512 is configured to hold instructions even when power is cut to the non-volatile storage device.

Aspects of logic processor 504, volatile memory 508, and non-volatile storage device 512 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The term "program" may be used to describe an aspect of computing system 500 implemented to perform a particular function. In some cases, a program may be instantiated via logic processor 504 executing instructions held by non-volatile storage device 512, using portions of volatile memory 508. It will be understood that different programs may be instantiated from the same application, service, code block, object, library, routine, API, function, etc. Likewise, the same program may be instantiated by different applications, services, code blocks, objects, routines, APIs, functions, etc. The term "program" encompasses individual or groups of executable files, data files, libraries, drivers, scripts, database records, etc.

When included, display subsystem 516 may be used to present a visual representation of data held by non-volatile storage device 512. As the herein described methods and processes change the data held by the non-volatile storage device, and thus transform the state of the non-volatile storage device, the state of display subsystem 516 may likewise be transformed to visually represent changes in the underlying data. Display subsystem 516 may include one or more display devices 18 utilizing virtually any type of technology. Such display devices 18 may be combined with logic processor 504, volatile memory 508, and/or non-volatile storage device 512 in a shared enclosure, or such display devices 18 may be peripheral display devices.

When included, input subsystem 520 may comprise or interface with one or more user-input devices. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone 260 for speech and/or voice recognition; an infrared, color, stereoscopic, and/or depth camera for machine vision and/or gesture recognition; a head tracker, eye tracker, accelerometer 232, and/or gyroscope 236 for motion detection, gaze detection, and/or intent recognition; electric-field sensing componentry for assessing brain activity; any of the sensors described above with respect to wearable mobile computing device 200; and/or any other suitable sensor.

When included, communication subsystem 524 may be configured to communicatively couple computing system 500 with one or more other computing devices. Communication subsystem 524 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 500 to send and/or receive messages to and/or from other devices via a network such as the Internet.

According to one aspect of the present disclosure, a method for estimating blood pressure is provided, comprising training a machine learning model on a cohort data set. The cohort data set may include subject-specific contextual data, time-varying features, and blood pressure measurements for a plurality of subjects. The method may further include receiving contextual data for a specific subject, wherein the contextual data includes medical history data of the subject. The method may include personalizing the machine learning model to the subject based on the contextual data. In addition, the method may further include calibrating the machine learning model to the subject based on a set of time-varying features and blood pressure measurements of the subject. The method may further include using the machine learning model and the time-varying features for the subject to generate a blood pressure estimate.

In this aspect, the contextual data of the subject may include information from the subject's medical history data selected from the set consisting of demographic information, comorbidities, past and present medications, vital signs, laboratory test results, recent weight change, echocardiogram results, cardiovascular disease history, smoking history, and past and present pregnancy.

In this aspect, the subject-specific contextual data may be used to determine parameters of the machine learning model.

In this aspect, the machine learning model may be calibrated at least in part using a brachial cuff measurement.

In this aspect, the machine learning model may be calibrated at least in part by the subject going through a series of perturbations based on posture.

In this aspect, the machine learning model may be calibrated at least in part by the subject exercising at varying levels of intensity.

In this aspect, the machine learning model may be calibrated at least in part by the subject taking medication which changes the blood pressure of the subject.

In this aspect, the blood pressure estimate may be conveyed for display on a display device.

In this aspect, the time-varying features for the subject may be detected by a wearable sensing device.

In this aspect, the wearable sensing device may include an electrocardiograph (EKG).

In this aspect, the wearable sensing device may include a pulse pressure sensor.

In this aspect, the pulse pressure sensor may be configured to detect the pressure wave morphology of the pulse pressure wave signal, including pressure wave morphology metrics selected from a group consisting of augmentation index, maximum systolic slope, systolic rise time, ejection time, dicrotic notch height, dicrotic notch time, pulse pressure, reflected wave arrival time, and heart rate.

In this aspect, the wearable sensing device may include both a pulse pressure sensor and an EKG, wherein the wearable sensing device is configured to determine a pulse arrival time using the pulse pressure sensor and EKG, and the time-varying information includes the pulse arrival time.

According to another aspect of the present disclosure, a wearable sensing device is provided, comprising a processor configured to receive contextual data for a specific subject. The contextual data may include medical history data of the subject. The processor may be further configured to receive a cohort data set. The cohort data set may include subject-specific contextual data, time-varying features, and blood pressure measurements for a plurality of subjects. The processor may be configured to detect a pulse pressure wave signal using a pulse pressure sensor. The processor may be further configured to determine a blood pressure estimate using a machine learning model that takes as inputs at least the contextual data of the subject, the cohort data set, and a set of time-varying features for the subject including the pulse pressure wave signal.

In this aspect, the processor may be configured to detect a pulse electrical signal using an electrocardiograph (EKG).

In this aspect, the set of time-varying features for the subject may include a pulse arrival time. The pulse arrival time may be determined using the pulse pressure wave signal and the pulse electrical signal.

In this aspect, the contextual data for the subject may include medical history data of the subject selected from the group consisting of demographic information, comorbidities, past and present medications, vital signs, laboratory test results, recent weight change, echocardiogram results, cardiovascular disease history, smoking history, and past and present pregnancy.

In this aspect, the pulse pressure sensor may be configured to detect the pressure wave morphology of the pulse pressure wave signal, including pressure wave morphology metrics selected from a group consisting of augmentation index, maximum systolic slope, systolic rise time, ejection time, dicrotic notch height, dicrotic notch time, pulse pressure, reflected wave arrival time, and heart rate.

In this aspect, the blood pressure estimate is conveyed for display on a display device.

According to another aspect of the present disclosure, a wearable sensing device is provided, comprising a processor configured to receive contextual data for a specific subject. The contextual data may include medical history data of the subject. The processor may be configured to receive a set of blood pressure measurements of the subject. The processor may be further configured to receive a cohort data set. The cohort data set may include subject-specific contextual data, time-varying features, and blood pressure measurements for a plurality of subjects. The processor may be configured to detect a set of time-varying features for the subject including a pulse pressure wave signal. The processor may be further configured to determine a blood pressure estimate at least in part by inputting at least the contextual data of the subject, the cohort data set, the set of blood pressure measurements of the subject, and the set of time-varying features for the subject into a machine learning model. Determining the blood pressure estimate may further include personalizing the machine learning model to the subject based on the contextual data. In addition, determining the blood pressure estimate may include calibrating the machine learning model to the subject based on a set of time-varying features and the blood pressure measurements of the subject. Determining the blood pressure estimate may further include using the machine learning model and the time-varying features for the subject to generate a blood pressure estimate.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A method for estimating blood pressure, comprising:
training a machine learning model on a cohort data set, wherein the cohort data set includes subject-specific contextual data, time-varying features, and blood pressure measurements for a plurality of subjects;
receiving contextual data for a specific subject, wherein the contextual data includes medical history data of the subject;
personalizing the machine learning model to the subject based on the contextual data;
detecting a pulse pressure wave signal of the subject over time using a pulse pressure sensor of a wearable sensing device;
calibrating the machine learning model to the subject based on a set of time-varying features for the subject including the pulse pressure wave signal detected during an initial period of time, and blood pressure measurements of the subject; and
using the machine learning model following calibration and the time-varying features for the subject including the pulse pressure wave signal detected during a subsequent period of time to generate a blood pressure estimate.

2. The method of claim 1, wherein the contextual data of the subject includes information from the subject's medical history data selected from the set consisting of demographic information, comorbidities, past and present medications, vital signs, laboratory test results, recent weight change, echocardiogram results, cardiovascular disease history, smoking history, and past and present pregnancy.

3. The method of claim 1, wherein the subject-specific contextual data is used to determine parameters of the machine learning model.

4. The method of claim 1, wherein the machine learning model is calibrated at least in part using a brachial cuff measurement.

5. The method of claim 1, wherein the machine learning model is calibrated at least in part by the subject going through a series of perturbations based on posture.

6. The method of claim 1, wherein the machine learning model is calibrated at least in part by the subject exercising at varying levels of intensity.

7. The method of claim 1, wherein the machine learning model is calibrated at least in part by the subject taking medication which changes the blood pressure of the subject.

8. The method of claim 1, wherein the blood pressure estimate is conveyed for display on a display device.

9. The method of claim 1, wherein the wearable sensing device includes an electrocardiograph (EKG).

10. The method of claim 1, wherein the pulse pressure sensor is configured to detect a pressure wave morphology of the pulse pressure wave signal, including pressure wave morphology metrics selected from a group consisting of augmentation index, maximum systolic slope, systolic rise time, ejection time, dicrotic notch height, dicrotic notch time, pulse pressure, reflected wave arrival time, and heart rate.

11. The method of claim 1, wherein the wearable sensing device includes both the pulse pressure sensor and an EKG, wherein:
the wearable sensing device is configured to determine a pulse arrival time using the pulse pressure sensor and EKG; and
the time-varying information includes the pulse arrival time.

12. A wearable sensing device, comprising:
a processor configured to:
receive contextual data for a specific subject, wherein the contextual data includes medical history data of the subject;
receive a cohort data set, wherein the cohort data set includes subject-specific contextual data, time-varying features, and blood pressure measurements for a plurality of subjects;
detect a pulse pressure wave signal of the subject over time using a pulse pressure sensor of a wearable sensing device;
calibrate a machine learning model to the subject based on a set of time-varying features for the subject including the pulse pressure wave signal detected during an initial period of time, and blood pressure measurements of the subject; and
determine a blood pressure estimate using the machine learning model following calibration that takes as inputs at least the contextual data of the subject, the cohort data set, and the set of time-varying features for the subject including the pulse pressure wave signal detected during a subsequent period of time.

13. The wearable sensing device of claim 12, wherein the processor is configured to detect a pulse electrical signal using an electrocardiograph (EKG).

14. The wearable sensing device of claim 13, wherein the set of time-varying features for the subject includes a pulse arrival time, wherein the pulse arrival time is determined using the pulse pressure wave signal and the pulse electrical signal.

15. The wearable sensing device of claim 12, wherein the contextual data for the subject includes medical history data of the subject selected from the group consisting of demographic information, comorbidities, past and present medications, vital signs, laboratory test results, recent weight change, echocardiogram results, cardiovascular disease history, smoking history, and past and present pregnancy.

16. The wearable sensing device of claim 12, wherein the pulse pressure sensor is configured to detect the pressure wave morphology of the pulse pressure wave signal, including pressure wave morphology metrics selected from a group consisting of augmentation index, maximum systolic slope, systolic rise time, ejection time, dicrotic notch height, dicrotic notch time, pulse pressure, reflected wave arrival time, and heart rate.

17. The wearable sensing device of claim 12, wherein the blood pressure estimate is conveyed for display on a display device.

18. A wearable sensing device, comprising:
a processor configured to:
receive contextual data for a specific subject, wherein the contextual data includes medical history data of the subject;
receive a set of blood pressure measurements of the subject;
receive a cohort data set, wherein the cohort data set includes subject-specific contextual data, time-varying features, and blood pressure measurements for a plurality of subjects;
detect a set of time-varying features for the subject including a pulse pressure wave signal of the subject detected over time using a pulse pressure sensor of a wearable sensing device; and
determine a blood pressure estimate at least in part by:
inputting at least the contextual data of the subject, the cohort data set, the set of blood pressure measurements of the subject, and the set of time-varying features for the subject into a machine learning model;
personalizing the machine learning model to the subject based on the contextual data;
calibrating the machine learning model to the subject based on a set of time-varying features for the subject including the pulse pressure wave signal detected during an initial period of time, and the blood pressure measurements of the subject; and
using the machine learning model following calibration and the time-varying features for the subject including the pulse pressure wave signal detected during a subsequent period of time to generate a blood pressure estimate.

* * * * *